United States Patent [19]

Wehrenberg

[11] Patent Number: 5,648,525
[45] Date of Patent: Jul. 15, 1997

[54] METHOD FOR PREPARATION OF HERBICIDE INTERMEDIATES

[75] Inventor: Peter K. Wehrenberg, Daphne, Ala.

[73] Assignee: Zeneca Limited, London, England

[21] Appl. No.: 552,028

[22] Filed: Nov. 2, 1995

[51] Int. Cl.$^6$ .................................................. C07C 315/00
[52] U.S. Cl. .................................................. 562/429
[58] Field of Search .................................................. 562/429

[56] References Cited

U.S. PATENT DOCUMENTS 4,704,467  11/1987  Wehrenberg .

OTHER PUBLICATIONS

R.A. Rossi et al., "Photostimulated Arylation of Cyanomethyl Anion by the SRN1 Mechanism of Aromatic Substitution," *J. Org. Chem.*, vol. 41, No. 21, pp. 3371–3373, 1976; Columbus, OH.

J.F. Bunnett, "Aromatic Substitution by the SRN1 Mechanism" *Accounts of Chemical Research*, vol. 11, pp. 413–420, 1978; Columbus, OH.

J.D. Loudon, "The Action of Sulphinates on 2:4–Dinitrodiphenylsulphones," *Journal of the Chemical Society*, pp.218–222, 1936, London.

Helvetica Chimca Acta, vol 68, pp. 846–853, Fischer et al 1985.

Helvetica Chimca Acta, vol 68, pp. 854–859, Fischer et al 1985.

*Primary Examiner*—Samuel Barts
*Attorney, Agent, or Firm*—Joseph R. Synder

[57] ABSTRACT

A method for the preparation of 2-(substituted)-4-methylsulfonylbenzoic acid by reacting a 2-(substituted)-4-nitrobenzoic acid with sodium methyl sulfinate.

7 Claims, No Drawings

METHOD FOR PREPARATION OF HERBICIDE INTERMEDIATES

BACKGROUND OF THE INVENTION

This invention relates to a method for preparing 2-(substituted)4- methylsulfonyl benzoic acids which are useful in the preparation of certain 2-(chloro, bromo or nitro)-4-methylsulfonyl-benzoyl -1,3-cyclohexanedione herbicides, such as those described in U.S. Pat. No. 4,946,981 and U.S. Pat. No. 5,006,158. The 2-(substituted)-4-methylsulfonyl benzoic acids may be converted to their acid chloride, as described in U.S. Pat. No. 5,008,448. The resulting acid chloride or cyanide can then be reacted with certain 1,3-cyclohexanediones according to the process of U.S. Pat. No. 4,695,673 or U.S. Patent No. 4,708,127.

U.S. Pat. No. 4,704,467 teaches a method of preparing a mercaptobenzoate of the formula

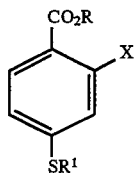

wherein R is alkyl, $R^1$ is alkyl or aryl and X is halogen or nitro, including reacting a compound of the formula

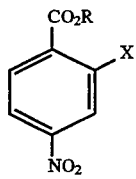

wherein R, and X are as defined above, with a mercaptan having the formula R-SH in the presence of an inorganic base, a phase transfer catalyst and a non-polar aprotic solvent.

The mercaptobenzoate may then be converted to its corresponding alkylsulfonyl benzoic acid.

It has now been surprisingly found that reacting a 2-(substituted)-4-nitrobenzoic acid with sodium methyl sulfinate can generate a 2-(substituted)-4-methylsulfonyl benzoic acid. This reaction is more favorable than the procedure in U.S. Pat. No. 4,704,467 for two reasons. First, the instant invention may be carried out using the benzoic acid and not the benzoate, thus saving a hydrolysis step, (and usually an esterification step because the alkylbenzoate is typically prepared from the acid). Second, because the instant method produces the sulfone directly, no additional oxidation step is necessary to produce the same from the mercaptan.

SUMMARY OF THE INVENTION

According to one embodiment of the invention, there is provided a process for preparing a compound of the formula

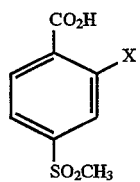

wherein X is halogen or nitro, including the steps of:
a) reacting a 2-(substituted)-4-nitrobenzoic acid with sodium methyl sulfinate; and
b) heating the mixture.

In another embodiment, there is provided a process for preparing a compound of the formula

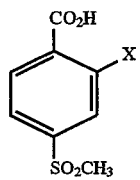

wherein X are as defined above, including the steps of:
a) reacting a 2-(substituted)-4-nitrobenzoic acid with sodium methyl sulfinate; and
b) irradiating the mixture with an ultraviolet (UV) light source.

DETAILED DESCRIPTION OF THE INVENTION

The process of this invention allows the displacement of the 4-nitro group of a 2-(substituted)-4-nitrobenzoic acid using sodium methyl sulfinate to generate a 2-(substituted) -4-methylsulfonylbenzoic acid. The invention process is schematically represented as follows:

SCHEME 1

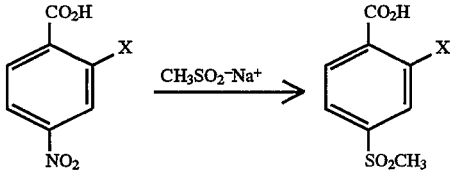

wherein X is halogen or nitro.

According to this invention, a 2-(substituted)-4-nitrobenzoic acid is reacted with sodium methyl sulfinate to give the 2-(substituted)-4-(methylsulfonyl) benzoic acid product of Scheme 1. The preferred product is 2-(nitro)-4-(methylsulfonyl) benzoic acid and the preferred starting material is 2,4-dinitrobenzoic acid. The term "halogen" includes chlorine and bromine.

In one embodiment of this invention, the reaction in Scheme 1 is carried out by nucleophilic substitution. This is a photostimulated reaction that may be carried out in a photochemical reactor equipped with a UV lamp, or some other reaction procedure with exposure to a UV light source.

In a typical photostimulated reaction, a molar excess of sodium methyl sulfinate is reacted with a 2-(substituted)-4-nitrobenzoic acid dissolved in a low molecular weight alcohol. A 2:1 molar ratio of sodium methyl sulfinate to a 2-(substituted)-4- nitrobenzoic acid is preferred. Methanol and ethanol are preferred alcohols. The mixture is irradiated using a UV light source for about 1–4 hours.

The reaction is run at temperatures from about 0° to about 70° C. depending on the solvent used. The preferred temperature is from about 15° to about 30° C. The reaction can be run at sub-atmospheric or super-atmospheric pressure, however atmospheric pressure is preferred.

After the requisite reaction time, an aliquot of the reaction mixture is removed and acidified with 1N HCl. Methylene chloride is added, or some other suitable organic solvent, and the reaction mixture is shaken. The organic layer is removed, dried and analyzed by a suitable analytical technique such as gas chromatography or high pressure liquid chromatography to monitor product formation.

In a second embodiment of this invention, a 2-(substituted)-4-nitrobenzoic acid and sodium methyl sulfinate are reacted in about an equal molar ratio or wherein the sodium sulfinate is in excess. The reactants are dissolved in a polar solvent such as dimethyl sulfoxide. The reaction can be run at sub-atmospheric or super-atmospheric pressure, however atmospheric pressure is preferred. The reaction mixture is heated to about 50° to 150° C. and preferably from 50°–100° C. The reaction is run from about 1 to 20 hours. The reaction may be carrried out utilizing a catalyst such as cuprous chloride.

After the requisite reaction time, an aliquot of the reaction mixture is removed and acidified with 1N HCl. Methylene chloride is added, or some other suitable organic solvent, and the reaction mixture is shaken. The organic layer is removed, dried and analyzed by a suitable analytical technique such as gas chromatography or high pressure liquid chromatography to monitor product formation.

In a third embodiment of this invention, an equal molar ratio of sodium methyl sulfinate is reacted with a 2-(substituted)-4-nitrobenzoic acid. The amount of sodium methyl sulfinate may be in excess. A solvent is used to dissolve the reactants such as ethylene glycol or ethanol but other suitable solvents include $C_2$-$C_6$ alkanols. The reaction can be run at sub-atmospheric or super-atmospheric pressure, however atmospheric pressure is preferred.

The reaction mixture is heated to reflux temperature, said temperature being solvent dependent. The preferred solvents are ethylene glycol and ethanol. If ethylene glycol is used, the preferred temperature is between 100° C. to 150° C. If ethanol is used, the preferred temperature is between 50° C. to 100° C. The reaction is carried out under an inert atmosphere such as nitrogen, but other inert gases are also suitable. The reaction is run for about 1 to 20 hours.

After the requisite reaction time, an aliquot of the reaction mixture is removed and acidified with 1N HCl. Methylene chloride is added, or some other suitable organic solvent, and the reaction mixture is shaken. The organic layer is removed, dried and analyzed by a suitable analytical technique such as gas chromatography or high pressure liquid chromatography to monitor product formation.

The following non-limiting series of examples illustrate the method of the present invention.

EXAMPLE 1

To a round bottom flask were added 4.24g (20 mmol ) of 2,4 dinitrobenzoic acid, 2.05 g of sodium methyl sulfinate (20 retool) and 10 mL of ethanol. The reaction mixture was heated to reflux under a $N_2$ atmosphere. After about 18 hours of reflux, a sample of the reaction mixture was partitioned between 1 N HCl and methylene chloride. The methylene chloride layer was removed, solvent evaporated and the residual product silylated. The silylated product was injected into a gas chromatograph. The product was confirmed with an authentic sample of the product.

EXAMPLE 2

To a 25 mL round bottom flask equipped with a magnetic stir bar, under $N_2$ atmosphere were added 50 mL of dimethyl sulfoxide and 2.0 g of cuprous chloride (20 retool) to give a green suspension. The reaction mixture was heated to 90° C. in an oil bath. At this point, 2.05 g of sodium methyl sulfinate (20 mmol) was added and heating was continued. After 15 minutes, a very thick brown paste had developed. The reaction mixture was transferred to a three necked 100 mL round bottom flask with a thermometer, $N_2$ gas bubbler and magnetic stir bar. The mixture was now a stirable brown slurry. The reaction was heated to 90° C. and 4.24 g of 2,4-dinitrobenzoic acid (20 retool) was added.

After about 2 hours, a 80 microliter aliquot was removed from the reaction mixture, 1 mL of 1N HCl and 1 mL of methylene chloride were added. The organic layer was removed, solvent evaporated in a stream of compressed air and 1 mL of a silylating agent was added. The aliquot was gas chromatographed showing product formation. The product was confirmed with an authentic sample of the product.

EXAMPLE 3

To a 25 mL round bottom flask equipped with a stir bar were added 4.24 g of 2,4-dinitrobenzoic acid (20 retool), 2.08 g of sodium methyl sulfinate (40 mmol) and 10 mL of dimethyl sulfoxide and the reaction mixture was heated to 50 ° C. After about 18 hours of reaction time, HPLC analysis indicates some reaction product. The product was confirmed with an authentic sample of the product.

EXAMPLE 4

To a 5 millimeter nuclear magnetic resonance (NMR) tube were added, 150 mg of 2,4-dinitrobenzoic acid (0.707 mmol), 154 mg of sodium methyl sulfinate (1.50 mmol) and 1 mL of dimethyl sulfoxide. The reaction mixture was irradiated by placing the tube approximately 5 centimeters from a Hanova quartz high pressure Hg are lamp, using a quartz immersion well, with water circulating through it and a Pyrex sleeve filter. After about 18 minutes, the reaction was orange and cloudy.

After 1 hour, an aliquot was removed from the NMR tube and partitioned between 1N HCl and methylene chloride. The methylene chloride was removed, and the residue silylated. HPLC indicated some formation of the product. The product was confirmed by comparison of the NMR spectrum with that of an authentic sample of the product.

Although the invention has been described with reference to the preferred embodiments and examples thereof, the scope of the present invention is not limited only to these described embodiments. As will be apparent to persons skilled in the art, modifications and adaptations to the above described invention can be made without departing from the spirit and scope of the invention, which is defined and circumscribed by the appended claims.

What is claimed is:

1. A method of making a compound of the formula

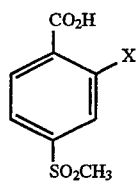

wherein X is halogen or nitro, comprising the steps of:
   a) reacting a 2-(substituted)-4-nitrobenzoic acid with sodium methyl sulfinate; and
   b) heating the mixture.

2. A method according to claim 1 wherein the 2-(substituted)-4-nitrobenzoic acid is reacted with sodium methyl sulfinate in the presence of cuprous chloride.

3. A method according to claim 1 wherein X is chlorine.

4. A method according to claim 1 wherein X is nitro.

5. A method of making a compound of the formula

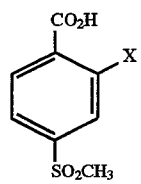

wherein X is halogen or nitro, comprising the steps of:
   a) reacting a 2-(substituted)-4-nitrobenzoic acid with sodium methyl sulfinate; and
   b) irradiating the mixture with a UV source.

6. A method according to claim 5 wherein X is chlorine.

7. A method according to claim 5 wherein X is nitro.

* * * * *